United States Patent [19]

Juvin et al.

[11] Patent Number: 4,518,593

[45] Date of Patent: May 21, 1985

[54] INSECTICIDE COMPOSITION FOR USE IN THE FORM OF A SHAMPOO

[75] Inventors: Pierre Juvin, Neuilly-sur-Seine; Pierre Moreau, Limoges, both of France

[73] Assignee: S.E.R.T.O.G., France

[21] Appl. No.: 572,956

[22] Filed: Jan. 23, 1984

Related U.S. Application Data

[63] Continuation of Ser. No. 192,800, Oct. 1, 1980, abandoned, which is a continuation of Ser. No. 853,965, Nov. 22, 1977, abandoned.

[51] Int. Cl.$^3$ ............................................. A61K 35/78
[52] U.S. Cl. .................................................. 424/195
[58] Field of Search ........................................ 424/195

[56] References Cited

U.S. PATENT DOCUMENTS 2,788,308  4/1957  Ochs et al. ........................... 424/317
3,634,264  1/1972  Pence .................................... 424/70

FOREIGN PATENT DOCUMENTS 2212115  9/1973  Fed. Rep. of Germany ...... 424/317

OTHER PUBLICATIONS

King, "Chemicals Evaluated as Insecticides and Repellents", Agriculture Handbook No. 69, 1954.
J. of Econ. Ent. vol. 18, pp. 292–299, (1925).

Primary Examiner—Leonard Schenkman
Assistant Examiner—John W. Rollins, Jr.
Attorney, Agent, or Firm—Sughrue, Mion, Zinn, Macpeak, and Seas

[57] ABSTRACT

The present invention relates to an insecticide composition for use in the form of a shampoo, which comprises a wetting agent and 1 to 25% by volume of at least one organic acid having 2 to 8 carbon atoms such that the pH of the composition is less than 4.5.

3 Claims, No Drawings

INSECTICIDE COMPOSITION FOR USE IN THE FORM OF A SHAMPOO

This application is a continuation of application Ser. No. 192,800, filed Oct. 1, 1980, now abandoned which is a continuation of Ser. No. 853,965, filed Nov. 22, 1977, now abandoned.

This invention relates to an insecticide composition for use especially as a shampoo, and intended in particular for destroying and repelling particularly resistant insects such as lice and fleas.

Various constituents are known which are capable of destroying these types of insects, as for example D.D.T., hexachlorocyclohexane and lindane. However, these substances are generally available as a powder, and their high toxicity makes it dangerous to use them in direct contact with the skin of mammals.

Taking as an example lice and fleas, these pests preferably attack young animals (children, puppies and kittens), namely those which are particularly sensitive to toxic substances.

On the other hand, it is known that certain acid constituents in liquid form such as acetic acid are active against insects and parasites, in particular when used in concentrated solution with a pH of around 2.

However, at such pH values, these liquid substances substantially attack the skin of animals to the extent that they have to be used in dilute solution, which substantially reduces their efficiency.

The object of the present invention is an insecticide composition which mitigates or overcomes these drawbacks, and which by its action both enables the insects and parasites to be effectively destroyed and prevents their return to the treated parts.

The composition of the present invention, to be used in particular as a shampoo, comprises a proportion of a wetting agent such as those selected from the group consisting of ammonium, triethanolamine and sodium lauryl sulphate, and comprises 1 to 25% by volume of at least one organic acid having 2 to 8 carbon atoms, such that the pH of the composition is less than 4.5 and preferably less than 3.5.

In particular, the compositions according to the invention may comprise 2 to 12% of acetic acid by volume, plus 0.5 to 20%, and in particular 0.5 to 3%, by volume of insecticides and/or parasiticides deriving from natural substances or those obtained artificially by synthesis, such as extracts or essences of clove, lavender, peppermint, origanum, rosemary, lime, juniper, lemon, citronella, thyme, Datura Stramonium, pine, pyrethrum or pyrethrin, and essential oils of peel or Ceylon cinnamon leaves.

The composition may also advantageously contain an insecticide and healing substance such as natural or synthetic camphor in a proportion by volume of 1.5 to 5%, and preferably 0.5 to 1.5%.

For a better understanding of the advantages and the mode of action of the composition according to the invention, a description is given hereinafter of non-limiting examples of formulations corresponding to the main applications of the composition, together with examples of the treatment carried out.

For each formulation, it will be noted that the proportion of wetting agent is important.

In this respect it has been surprisingly found that the insecticide effect of acetic acid is considerably increased by the addition of wetting agents such as those selected from the group consisting of ammonium, triethanolamine and sodium lauryl sulphate traditional cationic bases or non-ionic products used traditionally in the shampoo field.

This observation may be verified by the following test carried out on weevils, ants, earwigs: the product used in the examples described hereinafter is diluted to a third of its volume, and a few drops are placed on each insect held in an object slide so that the body of the insect is impregnated over approximately three quarters.

The time required for the insect to show no further movement is then measured. This time is compared with that obtained when using an aqueous solution of acetic acid of an equivalent pH.

The results obtained show that the times are on an average 2 to 5 times less for the shampoo than for the pure acetic acid (20 to 50 seconds instead of 1 to 3 minutes).

FIRST EXAMPLE

HYGIENIC SHAMPOO EFFECTIVE AGAINST LICE, FOR ADULTS AND CHILDREN

The proportions are by volume.
Texapant (R) N 40 (sodium lauryl sulphate) wetting agent (HENKEL) diluted to 30%: 75 to 95%
Synthetic camphor: 0.5 to 1.5%
Citronella: 0.5 to 1.5%
Acetic acid: 5 to 10%
pH: 1.8 to 2.3.

Case 1: Two children aged respectively 11 and 13 with hair comprising a considerable colony of adult lice and nits were treated with a shampoo containing 1% of synthetic camphor, 1% of citronella essence, 5% of acetic acid and 93% of Texapant (R) diluted to 30% (pH adjusted to 2.1).

The shampoo wash was carried out at 9 o'clock in the morning. The shampoo was used actively for 15 minutes, followed by a water wash.

An examination of the head showed that there were no longer any adult lice, and the proportion of nits was reduced.

Further shampooing was carried out 2, 4 and 6 days later although no adult louse was observed. The number of nits continuously decreased.

New washes were made every week. After three weeks the nits had totally disappeared.

Case 2: A young girl aged 15 observed on taking a bath that lice were swimming close to her. She was then treated each evening with a 0.8% lindane powder, she was covered with a bonnet all night and was then washed with an ordinary shampoo each morning and combed with a tooth comb. After five days, nits were still in her hair.

A single shampooing with the product indicated for case 1 was sufficient to clear her hair of all parasites and allow the previous fastidious and disagreeable treatment to be discontinued.

Case 3: A small 5 year old girl had been suffering from nits for three weeks and had been treated each evening with a powder comprising 0.4% lindane and 10% D.D.T. The insecticides were protected all night in her hair with a bonnet, and she was given an ordinary shampoo in the morning followed by combing with a tooth comb.

This little blonde girl had particularly fine hair, and the numerous nits were fixed very firmly thereto.

An initial treatment with the product of case 1 gave only a partial result. Two further applications of the product were necessary to totally eliminate the nits.

SECOND EXAMPLE

TREATMENT OF FLEAS, LICE AND TICKS ON DOGS

A shampoo was used containing 6% of acetic acid, 1.5% of citronella, 1.5% of clove essence and 91% of Texapant (R) diluted to 30% (pH adjusted to 2).

An adult Teckel dog infested with fleas was treated.

A wash with a shampoo of the above veterinary formula was carried out at 8 o'clock in the morning. By 12 o'clock the dog was free from fleas and contained no further fleas during the next three days in spite of an unfavourable environment.

A preservation treatment consisting of spraying a lotion in the form of a solution of 25% thyme decoction, 73% cider vinegar and 2% citronella enabled any return of the parasites to be prevented until the environment (premises and fabrics) had been completely disinfected with the products of Example 3.

THIRD EXAMPLE

TREATMENT OF PREMISES AND FABRICS

A shampoo was used composed of 10% acetic acid, 2% citronella essence and 2% camphor (pH adjusted to 1.8).

A proliferation of fleas had been noticed in a poorly closed room which had been unoccupied for some time, and contained various objects and fabrics.

After arranging the objects, the carpet covering part of the floor plus the tiling were sprayed with the shampoo diluted to twice its volume with water. Two hours later, the fleas gave no further sign of life.

In a like manner, coats, blankets and dog baskets were successfully treated with solutions of 5 cm$^3$ of shampoo per liter of water.

Generally, the method of using the products according to the invention is as follows: the parts to be treated are shampooed with the complexes described heretofore, the products are left to act for a time generally between one and ten minutes in the case of animals and five to twenty minutes in the case of objects.

Abundant rinsing is then carried out to wash away the acetic acids or its equivalents, together with the insects and parasites.

After washing, it is found that the products repulsive to insects remain in sufficient quantity to give protection against new infection.

However, in numerous cases, it is of advantage to continue treatment by means of successive washes at time intervals until the larva completely disappears, and to use a preservative treatment in the form of sprays of the various essences of insecticide or parasiticide products given heretofore, with or without camphor, but preferably without acetic acid, i.e. citronella, essence of clove, lavender, peppermint, origanum, rosemary, lime, juniper, lemon, thyme, Datura Stramonium, pyrethrum or essential oil of Ceylon cinnamon.

Such sprays protect the subject at length between each shampoo.

In addition, the insecticide action of the shampoo used in Case 1 of Example 1 was compared with a powder preparation containing 15% by weight of lindane in the following manner:

1. Test on the adult louse 5 cm$^3$ of pure shampoo were placed in a dish, and five lice (*Pediculus humanus*) were then placed therein. Death was immediate. In order to be certain of the result, a further test was carried out leaving the lice for only 10 seconds in the shampoo and withdrawing them with a wooden rod. They were then viewed under a lens and it was found that the lice were effectively dead.

The same test was carried out with shampoo diluted to 50%, then to 25%, so as to give concentrations varying from 25 to 100%.

The death of the lice was slower with the two dilutions, and the recovery test for the lice showed that after 30 seconds, the lice no longer returned to life.

The same tests were carried out on the *Phtirius pubis* species with the same 100% mortality after 30 seconds. These tests are compared with a 15% lindane powder preparation.

The table given hereinafter summarises the results obtained:

Tests on adult *Pediculus humanus*:

| | MORTALITY PERCENTAGE: | | |
|---|---|---|---|
| | After 10 seconds | After 30 seconds | After 2 hours |
| Pure R.S. 206 | 100% | 100% | 100% |
| R.S. 206 Diluted to 50% | 20% | 100% | 100% |
| R.S. 206 diluted to 25% | 0% | 100% | 100% |
| 15% lindane powder | 0% | 0% | 50% |

The same test was carried out on *Phtirius pubis* adults with identical results.

2. Test on the *Pediculus humanus* nit

It was very difficult to know if the nits had been properly killed by the product, because in order to be certain of their death it was necessary to wait two to five weeks. The fact of having separated the nit from the hair to which it was attached could have been the factor leading to its destruction.

The following test was carried out: ten hairs carrying nits were taken from a child and placed in dishes with the test products or water for time of 15 minutes, after which they were preserved at a temperature of 22°.

Some nits separated from the hair in the shampoo, whereas others remained attached. Observations were made over five weeks and the results were as follows:

| OBSERVATIONS ON THE HATCHING OF NITS: | | | | | |
|---|---|---|---|---|---|
| | 1st | 2nd | 3rd | 4th | 5th week |
| Pure R.S. 206 | 0 | 0 | 0 | 0 | 0 |
| R.S. 206 diluted to 50% | 0 | 0 | 0 | 0 | 0 |
| 15% lindane powder | 0 | 0 | 0 | 0 | 0 |

The same test was carried out on *Phtirius pubis* nits with identical results.

The product is thus more active than a 15% lindane formulation.

0.4 and 0.8% lindane formulations have insufficient action for use as a comparison element.

The bacteriostatic action of the products according to the invention was also verified even though they contain none of the normally used bactericides such as methyl paraoxybenzoate, and various tests have shown that no bacteria develops in the pure or 50% diluted product.

The test to check whether the preparation was free from bacteria was carried out because of the interesting results to be obtained.

The method employed was the following, using the shampoo of Example 1:

(1) Insemination on ordinary agar.

(2) Preservation in a drying cupboard at 37° C. for 48 hours and for seven days.

|  | After 48 hours | After 7 days |
|---|---|---|
| Results: | | |
| Pure shampoo | 0 colonies | 0 colonies |
| Shampoo diluted to 50% | 0 colonies | 0 colonies |
| After insemination with *escherichia coli*: | | |
| Pure shampoo | 0 colonies | 0 colonies |
| Shampoo diluted to 50% | 0 colonies | 0 colonies |

Other applications and modifications of the invention will be easily conceived by the expert of the art without leaving the scope of the invention, in particular by substituting equivalents for various products described heretofore, for example by replacing acetic acid with homologous acids, however it has been found that the results obtained may be substantially inferior, in particular with propionic and caprylic acid.

Finally, the determined toxicity may vary substantially, and this reinforces the advantage of acetic acid associated synergically with a wetting agent to give it an increased insecticide powder while maintaining its toxicity within limits entirely compatible with its use when in contact with sensitive epidermis.

In this respect, the P.O. toxicity obtained by administering the shampoo of Example 1 to male RIVER mice of an average weight of 25 grams shows the maximum tolerated dose to be 24 ml/kg and the lethal 100 dose to be 40 ml/kg.

The results do not enable a lethal 50 dose to be evaluated. By comparison, the lethal 50 dose for lindane observed with aqueous preparations administered orally to mice is approximately 300 mg/kg.

Finally, a study of local cutaneous tolerance showed a primary irritation index of 0.3, a low value, and repeated application tests on the ears of mice gave the conclusion that the shampoo is not an irritant. In addition, repeated applications on rabbits skin have shown an excellent tolerance.

Only tests in which eyes were involved suggest that the shampoo could be an irritant, but this irritating action is very weak when the product is used in its required dilution.

We claim:

1. A non-irritating insecticide composition for use in the form of a shampoo which comprises 74–95% by volume of a wetting agent selected from the group consisting of ammonium, triethanolamine and sodium lauryl sulphate, 2 to 12% by volume of acetic acid and 0.5 to 3% by volume of at least one natural or synthetic plant extract or essence selected from the group consisting of extracts and essences of clove, lavender, peppermint, origanum, rosemary, lime, juniper, lemon, citronella, thyme, Datura Stramonium, pine, pyrethrum, pyrethrin and Ceylon cinnamon leaves, the pH of the composition being less than 4.5.

2. An insecticide composition as claimed in claim 1, which comprises 0.5 to 3% by volume of citronella.

3. An insecticide composition as claimed in claim 1, wherein the wetting agent is sodium lauryl sulphate.

* * * * *